(12) United States Patent
Prestel (10) Patent No.: US 7,186,261 B2
(45) Date of Patent: Mar. 6, 2007

(54) MEDICAL FORCEPS (75) Inventor: Stephan Prestel, Rheinstetten-Moersch (DE)

(73) Assignee: Richard Wolf GmbH, Knittlingen (DE)

( * ) Notice: Subject to any disclaimer, the term of this patent is extended or adjusted under 35 U.S.C. 154(b) by 491 days.

(21) Appl. No.: 10/299,111

(22) Filed: Nov. 19, 2002

(65) Prior Publication Data
US 2003/0097147 A1 May 22, 2003

(30) Foreign Application Priority Data
Nov. 19, 2001 (DE) ................................ 101 56 313

(51) Int. Cl.
A61B 17/29 (2006.01)
(52) U.S. Cl. ..................................... 606/208
(58) Field of Classification Search ........ 606/205–209, 606/158, 40, 198; 600/564, 565
See application file for complete search history.

(56) References Cited

U.S. PATENT DOCUMENTS

| 4,522,206 | A | * | 6/1985 | Whipple et al. ............. 606/174 |
| 5,238,002 | A | * | 8/1993 | Devlin et al. ................ 600/564 |
| 5,263,967 | A | * | 11/1993 | Lyons et al. ................ 606/205 |
| 5,312,434 | A | | 5/1994 | Crainich |
| 5,368,606 | A | * | 11/1994 | Marlow et al. ............. 606/170 |
| 5,456,695 | A | * | 10/1995 | Herve Dallemagne ...... 606/207 |
| 5,472,439 | A | * | 12/1995 | Hurd .............................. 606/1 |
| 5,535,754 | A | * | 7/1996 | Doherty ....................... 600/564 |
| 5,556,404 | A | * | 9/1996 | Belanger et al. ............. 606/151 |
| 5,573,546 | A | * | 11/1996 | Nakao ......................... 606/205 |
| 5,609,599 | A | * | 3/1997 | Levin .......................... 606/153 |
| 5,630,832 | A | * | 5/1997 | Giordano et al. ........... 606/208 |
| 5,681,348 | A | | 10/1997 | Sato |
| 5,853,412 | A | * | 12/1998 | Mayenberger ............... 606/51 |
| 5,993,467 | A | | 11/1999 | Yoon |
| 6,378,351 | B1 | * | 4/2002 | Ouchi et al. .................. 72/336 |
| 2001/0037128 | A1 | | 11/2001 | Arambula |
| 2002/0058961 | A1 | * | 5/2002 | Aguilar et al. .............. 606/198 |
| 2002/0143358 | A1 | * | 10/2002 | Domingo et al. ........... 606/190 |

FOREIGN PATENT DOCUMENTS

| DE | 44 44 403 A1 | 6/1996 |
| DE | 296 14 931 U1 | 3/1997 |
| DE | 198 13 781 A1 | 10/1999 |
| DE | 199 06 360 A1 | 8/2000 |
| WO | WO 99/49794 A1 | 10/1999 |

* cited by examiner

Primary Examiner—Eduardo C. Robert
Assistant Examiner—Richard Shaffer
(74) Attorney, Agent, or Firm—Akin Gump Strauss Hauer & Feld, LLP (57) ABSTRACT A medical forceps is provided with a tubular outer shank, on whose distal end there is formed a forceps jaw with two jaw parts. The two jaw parts are each rotatably mounted on the outer shank at two sides opposite one another. A tubular inner shank for actuating the jaw parts is displaceably arranged in the inside of the outer shank in its longitudinal direction. The inner shank is coupled to the two jaw parts for their actuation via two lever systems. Each of the lever systems is linked to the two jaw parts, one lever system on each of the two opposite sides.

15 Claims, 6 Drawing Sheets

MEDICAL FORCEPS

CROSS REFERENCE TO RELATED APPLICATION

This application claims priority from German patent application 101 56 313.2, filed Nov. 19, 2001.

BACKGROUND OF THE INVENTION

The invention relates to a medical forceps.

There are known medical forceps, which comprise a hollow shank into which, for example, an optical system is applied. From German published patent application DE 44 44 403 A1 there is known, for example, a medical forceps which comprises a hollow shank on whose end there is arranged a pivotable forceps jaw part. The opening and closing of the forceps jaw part is effected via an inner shank longitudinally movable in the inside of the shank. This inner shank engages centrally on the upper side of the forceps jaw part. The forceps jaw part in the lower region is rotatably linked onto the outer shank on two sides. By displacing the inner shank in the longitudinal direction of the forceps shank, the point of engagement of the inner shank on the forceps jaw part is radially pivoted about the rotation point of the forceps jaw part, and in this manner the forceps jaw is opened or closed. In the open condition this has the effect that a rear end of the forceps jaw part pivots into the inside of the shank. In this way, when the forceps is open, the field of view for optics arranged in the inside of the inner shank is very greatly limited.

BRIEF SUMMARY OF THE INVENTION

It is the object of the invention to provide a medical forceps with which a large forceps force may be created and which permits as large a field of view as possible for optics arranged in the inside of the forceps shank.

The medical forceps according to the invention comprises a tubular outer shank on whose distal end there is formed a forceps jaw with two jaw parts. The tubular outer shank preferably has a circular cross section and the two jaw parts together likewise preferably form a circular cross section of essentially the same diameter as the outer shank. The two jaw parts are each rotatably mounted on the outer shank on two opposite sides, i.e., preferably two sides lying diametrically opposite one another. Furthermore, in the tubular outer shank there is arranged a tubular inner shank for actuating the jaw parts. The tubular inner shank extends in the longitudinal direction parallel to the outer shank. At the same time, the tubular inner shank preferably has an outer contour which is designed corresponding to the inner contour of the outer shank, so that the inner shank is slidingly guided in the inside of the outer shank. The inner shank is coupled to the two jaw parts for their actuation via two lever systems. The lever systems convert the movement of the inner shank in the longitudinal direction into a pivoting or rotational movement of the two jaw parts. For this purpose, each of the lever systems is linked to the jaw part, one on each of the two sides lying opposite one another. This means the lever systems for opening and closing the jaw parts are arranged on the same sides of the forceps on which the mountings for the pivotable jaw parts are also provided. The mounting and actuation elements for the jaw parts are thus extremely compact and arranged tightly next to one another. This permits the mounting and actuation elements for the jaw parts to be designed slim in profile and compactly. Since the lever systems are arranged laterally on the forceps, it is not necessary for the elements of the jaw parts or the lever systems to project into the inside of the outer or inner shank on opening the forceps jaw parts. This means the inner space of the inner shank, as well as the region located in front of the opening of the inner shank on its distal end, may be kept free even when the forceps jaw is open, in order to ensure the largest possible field of view for optics applied into the inner shank. By way of the linkage on both sides or the engagement of a lever system on each jaw part on both sides, one may furthermore transmit a large force onto the jaw parts, so that a large forceps force may be made available, for example for separating tissue parts. The arrangement of two jaw parts permits a very large angle of opening of the jaw part, whereby on the one hand, the gripping of difficultly accessible or large tissue parts is favored, and on the other hand, the field of view through the open forceps jaw is very large.

Preferably, the two jaw parts each comprise on each of the two sides opposite one another a linkage lever extending proximally in the longitudinal direction of the outer and inner shanks, each linkage lever being coupled to the inner shank via one of the two lever systems. The jaw part extends in the distal direction of the forceps proceeding from a mounting point on which the jaw parts are mounted on the outer shank. The linkage lever extends in the opposite direction, i.e., in the proximal direction, proceeding from the mounting point. The linkage levers are preferably designed as one piece with the associated jaw parts. For opening the jaw parts, the associated linkage lever must therefore be pivoted in the same rotational direction as the jaw parts. For this purpose, the linkage levers are connected to the inner shank via the lever systems. The linear movement of the inner shank in its longitudinal direction sets the lever systems into a pivoting movement of the linkage levers, which in turn pivot out the two jaw parts. These two jaw parts with the associated linkage levers thus have a course of movement similar to a scissors.

Preferably, the linkage levers and the lever system are arranged lying radially further outward than the inner circumference of the inner shank. Such an arrangement has the effect that the smallest inner diameter of the whole forceps which is available is defined by the inner diameter of the inner shank. Thus, optics may be introduced through the inside of the inner shank up to the distal end of the forceps and thus be brought very close to the distal end of the forceps jaw. Furthermore, the field of view of the optics is not compromised by components of the actuation mechanism for the jaw parts lying further inside. Thus, one may create a very large field of view, which ensures good observation possibilities on applying the forceps.

On the two sides opposite one another the two jaw parts are preferably each mounted on respective common rotational points on the outer shank. This arrangement reduces the number of the required rotational points and effects favorable lever ratios, which permit a large force transmission. Furthermore, this arrangement allows the forceps jaw to be completely closed, so that the two jaw parts bear on one another with their side edges facing.

The linkage levers are each usefully connected to the inner shank via a respective transmission lever. With a linear movement of the inner shank against the linkage levers, these transmission levers produce a torque about their point of rotation, which leads to the pivoting of the linkage levers and thus of the jaw parts connected thereto, for opening and closing the forceps jaw.

On a first end the transmission levers are each preferably rotatably connected to a respective linkage lever, and on a second end are each rotatably connected to the inner shank. In this manner, the linear movement of the inner shank may be converted into a pivoting or rotational movement of the linkage lever and of the jaw part connected thereto. With a linear movement of the inner shank, the respective transmission lever pulls or pushes the associated linkage lever in a direction tangential to its point of rotation, so that the linkage lever is pivoted about the point of rotation. On pivoting the linkage lever, its force engagement point at which the transmission lever engages is displaced. This displacement may be compensated on account of the rotatable linking of the transmission lever on the linkage lever and the inner shank.

Preferably, on the opposite sides of the inner shank the two respective transmission levers are connected to the inner shank at a common rotation or linkage point. This arrangement reduces the number of required rotational or linkage connections, whereby the assembly is simplified. Furthermore, one ensures a symmetrical actuation or movement of the transmission lever and thus also of the jaw parts. A uniform and reliable force transmission may therefore be ensured. According to the movement direction of the inner shank, the transmission levers push or pull on the linkage levers, whereby the jaw parts are pivoted. At the same time, the push or pull direction of the transmission levers runs at an angle to the longitudinal axis of the inner shank.

At the distal end of the inner shank there is preferably formed at least one radially outwardly projecting projection, which engages into a corresponding recess at the distal end of the outer shank, wherein the recess in the longitudinal direction of the outer and of the inner shank has a greater extension than the projection. This arrangement of projection and recess forms a linear guide of the inner shank in the outer shank in its longitudinal direction. Furthermore, on account of the play, which is defined by the length difference of the outer and inner shanks, one defines a limitation for the maximum linear movement of the inner shank in the outer shank. Such a limitation, on account of the coupling of the inner shank and jaw parts, thus likewise leads to a limitation of the angle of opening of the jaw parts. Additionally, this linear guiding of the inner shank in the outer shank ensures that the inner shank correspondingly co-rotates with a rotation of the outer shank about its longitudinal axis. In this manner, it is possible to rotatably arrange the outer and inner shank on the forceps grip, wherein the whole jaw region of the forceps, i.e., the distal end of the forceps with the forceps jaw, may be very simply rotated about its longitudinal axis by rotating the outer shank.

It is further preferred to form on the inner shank a projection on each of the sides opposite one another and for the outer shank to comprise two corresponding recesses into which the projections engage. In this manner, a precise guiding of the inner shank in the outer shank is achieved. Furthermore, a secure force transmission onto the inner shank may be ensured when rotating the outer shank. With the arrangement of the recess and projection on each of the two sides opposite one another, on which the mounting points as well as the lever systems are provided for pivoting the jaw parts, an extremely compact and slim arrangement of all guide or mounting and actuation elements is achieved. In this manner, the largest possible free space is created in the inside of the forceps in its distal end region. Furthermore, it is possible to provide openings or recesses in the outer and inner shank in their distal end region. By these measures the field of view for optics arranged in the inside of the forceps may be increased.

Preferably, the linkage levers of the two jaw parts on each of the sides opposite one another are designed such that the linkage lever of a first jaw part is formed lying radially further inward than the linkage lever of the second jaw part. This means that the two linkage levers are arranged lying over one another or overlapping one another in the radial direction, i.e., in the direction that connects the two opposite sides transverse to the longitudinal direction of the outer and inner shanks. This scissor-like arrangement of the levers permits an extremely slim and compact construction of the lever system for actuating the jaw parts.

The two actuation levers on each of the two sides opposite one another are further preferably arranged respectively lying radially over one another. The arrangement is preferably designed such that that a transmission lever which is connected to the linkage lever of the first jaw part lies in a plane with a linkage lever of the second jaw part, while a transmission lever which is connected to a linkage lever of the second jaw part lies in a plane with a linkage lever of the first jaw part. The linkage and transmission levers are thus arranged lying over one another or overlapping, displaced from one another. Thus, a parallelogram-like lever system is created by the linkage and transmission levers for the two jaw parts on each of the two sides opposite one another. This arrangement is extremely compact and may further transmit a large force from the inner shank onto the jaw parts, so that these may exert a large closing force which favors a separation of tissue parts.

Furthermore, the linkage levers of the two jaw parts, preferably on each of the two sides lying opposite one another, are designed such that, seen in the longitudinal direction of the outer shank in the closed condition of the forceps jaw, the free end of a linkage lever of the first jaw part extends in the extension of the second jaw part and the free end of a linkage lever of the second jaw part extends in the extension of the first jaw part. This means that with respect to the longitudinal axis of the inner and outer shanks, the linkage levers are bent at an angle or stepped to the longitudinal axis of the respective jaw part. Preferably, the linkage lever extends parallel to and displaced from the longitudinal direction of the associated jaw part, whereby the rotation point of the jaw part preferably lies essentially in the middle between the longitudinal axis of the linkage lever and the longitudinal axis of the jaw part. At the same time, the longitudinal axis of the linkage lever and the longitudinal axis of the jaw part run essentially parallel to the longitudinal axis of the outer and inner shanks. The longitudinal axis of the inner shank preferably lies essentially on a plane with the two rotation points on which the two jaw parts are linked on the outer shank. The two rotation points on which the transmission levers are pivotably mounted on the inner shank preferably lie in the plane of the longitduinal axis of the inner shank and of the points of rotation of the jaw parts. The end regions of the linkage levers, which are connected to the transmission levers, preferably lie outside this plane. In this manner, it is ensured that the longitudinal direction of the transmission levers, i.e., the direction of the force transmitted by the transmission levers, always runs at an angle to the longitudinal axis of the associated linkage lever and of the inner shank. In this manner, one may ensure that in each position of the forceps a secure pivoting of the jaw parts is possible and that the forceps may not jam.

In a preferred embodiment, an opening may be formed in at least one of the two jaw parts. Such an opening permits one to look through the forceps jaw from the inside of the forceps or the inner shank even when the forceps jaw is closed. In this manner, the positioning of the forceps during an operation may also be simplified when the forceps jaw is closed. The opening is preferably arranged in the middle of the jaw part spaced from its outer or cutting edge, so that furthermore, a secure grip or a reliable cutting or separation of tissue by the forceps is ensured.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
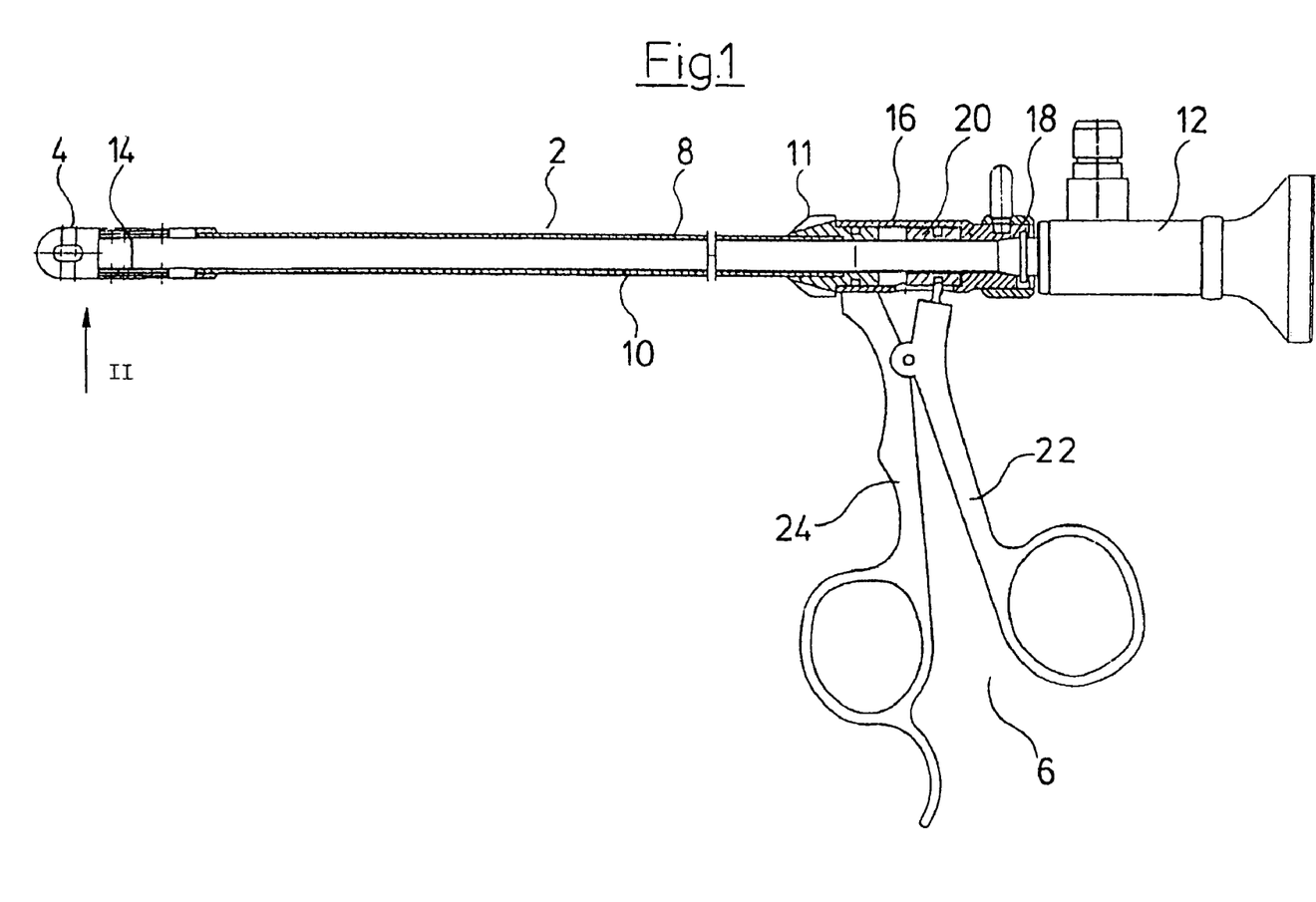
FIG. 1 is a sectional view of the medical forceps according to the invention.

FIG. 1 shows in a sectioned view the total view of the forceps according to the invention. The medical forceps comprises a forceps shank 2 at whose distal end there is arranged a forceps jaw 4 and at whose proximal end there is arranged a forceps handle 6. The forceps shank 2 consists of an outer shank 8 and of an inner shank 10 arranged in the inside of the outer shank. The outer shank 8 and the inner shank 10 are tubular, in particular formed with a circular cross section. At the same time the inner shank 10 has an outer diameter which essentially corresponds to the inner diameter of the outer shank 8. This permits the inner shank 10 to be guided in the outer shank 8 in a fitting manner and essentially free of play or with little play. The optics 12 extend from the proximal end of the forceps into the inner shank 10 and through this preferably up to the distal end 14 of the inner shank 10 in order to permit an observation of the region surrounding the forceps jaw 4 or of the region situated in front of the forceps jaw 4 during the operation.

At the proximal end of the forceps there is provided a forceps housing 16 proceeding from which the forceps shank 2 extends in the distal direction. In the forceps housing 16 at the distal end there is arranged a rotatable hand wheel 11 which is rigidly connected to the outer shank 8. The outer shank 8 may be rotated about its longitudinal axis by way of rotating the hand wheel 11. At the proximal end of the forceps housing 16 there is formed a cone receiver 18 in which the optics 12 may be releasably fixed. Furthermore a sliding sleeve 20 is arranged in the inside of the forceps housing 16. The sliding sleeve 20 is displaceable in the forceps housing 16 in the longitudinal direction of the outer shank 8 and of the inner shank 10. The sliding sleeve 20 is connected to the movable handle part 22 for actuating the sliding sleeve 20. The movable handle part 22 is pivotably mounted on the stationary handle part 24. The rigid handle part 24 is connected to the forceps housing 16. The sliding sleeve 20 is displaced in the axial direction, i.e. in the longitudinal direction of the forceps shank 2 in the forceps housing 16 by way of pivoting the movable handle part 22. The sliding sleeve 20 is rigidly connected to the inner shank 10. Thus the inner shank 10 is displaced in its longitudinal direction, i.e., in the axial direction of the forceps shank 2 in the outer shank 8, on actuation of the movable handle part 22.

Figure 2:
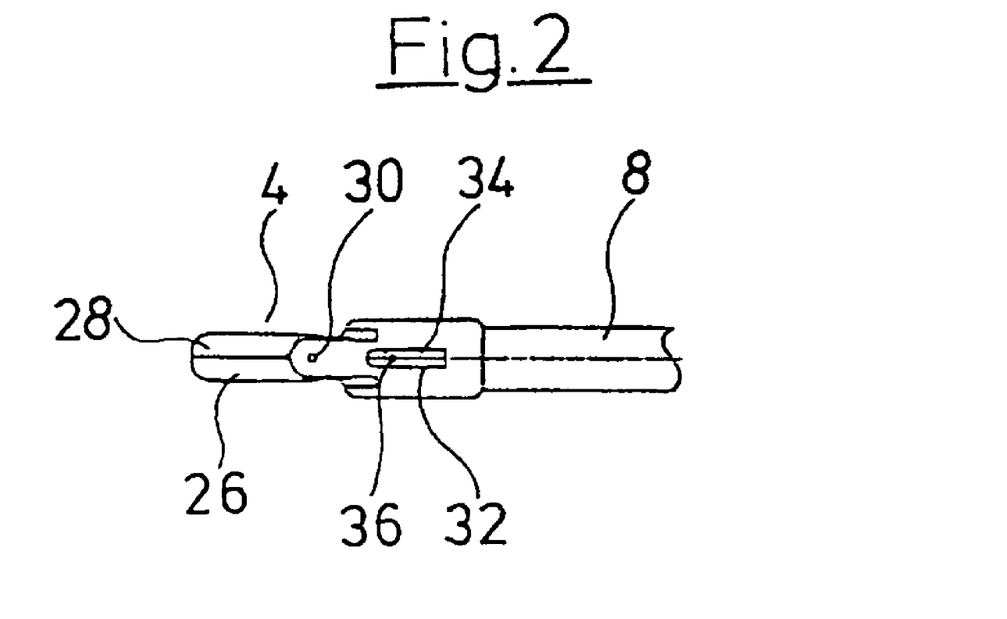
FIG. 2 is a detailed view of the forceps jaw in the closed condition taken in the direction II in FIG. 1.

FIG. 2 shows a detailed view of the forceps jaw 4 in the closed condition. FIG. 2 is a lateral view of the forceps jaw 4 in the direction of the arrow II in FIG. 1. The forceps jaw is formed by two jaw parts 26, 28. The two jaw parts 26 and 28 are formed spade or shell shaped so that together in the closed condition they likewise have an essentially tubular cross section. This means that the jaw parts 26 and 28 in the closed condition enclose a free space. The jaw parts 26 and 28 are rotatably mounted on two diametrically opposite sides on respective rotation points 30 on the outer shank 8. Furthermore, in the region of its distal end on the outer shank 8, there are formed longitudinal grooves 32, which extend in the longitudinal direction of the outer shank 8 on the respective diametrically opposite sides on which the rotation points 30 are also provided. Elongate projections 34 engage respectively into these longitudinal grooves 32. The projections 34 extend likewise in the longitudinal direction of the forceps shank 2 or of the outer shank 8. The projections 34 are rigidly formed in the region of the distal end 14 of the inner shank 10 and extend from this radially outward. The longitudinal grooves 32 in their longitudinal direction are formed longer than the projections 34 so that the projections are movable in the respective longitudinal grooves 32 in the longitudinal direction. In this manner the projections 34 and thus the inner shank 10 are guided in the longitudinal grooves with a movement in the longitudinal direction of the inner shank 10. Furthermore, the longitudinal grooves 32 have the effect that, on rotation of the outer shank 8 via the hand wheel 11, the inner shank 10 is correspondingly co-rotated, so that the complete forceps shank 2 with the forceps jaw 4 may be rotated with respect to the forceps housing 16 about the longitudinal axis of the forceps shank 2.

Figure 3:
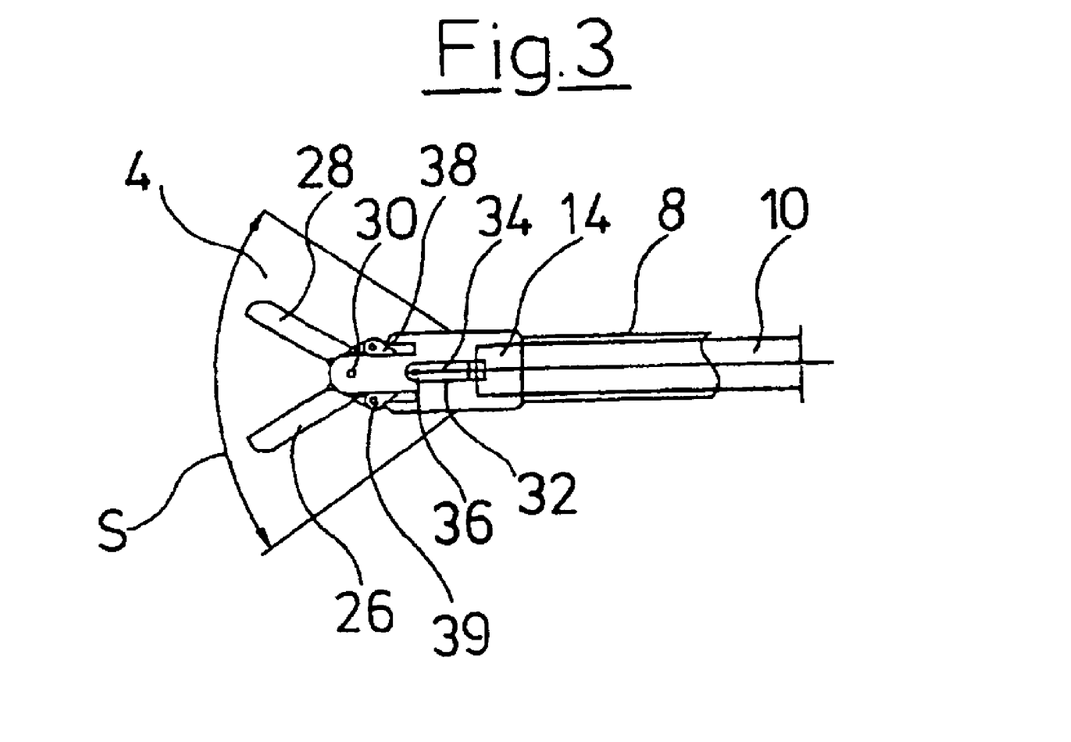
FIG. 3 is a detailed view of the forceps jaw in the open condition.

FIG. 3 shows a view of the forceps jaw 4 according to FIG. 2, wherein the forceps jaw 4 is opened. For opening the forceps jaw 4 the inner shank 10 is displaced in its longitudinal direction in the inside of the outer shank 8 in the distal direction. At the same time, the projections 34 are also displaced in the longitudinal grooves 32. With a suitable dimensioning of the length of the longitudinal grooves and the corresponding projections 34 the end faces of the longitudinal grooves and the projections may serve as abutments for limiting the movement of the inner shank 10 in its longitudinal direction. A linkage point 36 is respectively formed on each of the projections 34. In total therefore, there are provided two linkage points 36 on the two diametrically opposite sides of the forceps shank 2, on which the rotation points 30 are also arranged. The linkage points 36 each lie respectively with one of the rotation points 30 on a common axis, which extends parallel to the longitudinal axis of the forceps shank 2 on each side. On the linkage points 36 there are linked transmission levers 38 and 39 which pivot the jaw parts 26 and 28 about their rotation points 30. Furthermore, in FIG. 3 the maximal field of view S for optics arranged in the inside of the inner shank 10 is indicated. This field of view S extends proceeding from the distal end 14 of the inner shank 10. Such a large field of view S is made possible in that all mounting and actuation elements, i.e., the transmission levers 38, 39, the rotation points 30, as well as the linkage points 36, are arranged on two sides of the outer shank 8 diametrically opposite one another. This allows openings to be formed between these two opposite sides or side regions in the outer shank 8, which permit a correspondingly large field of view S.

Figure 4:
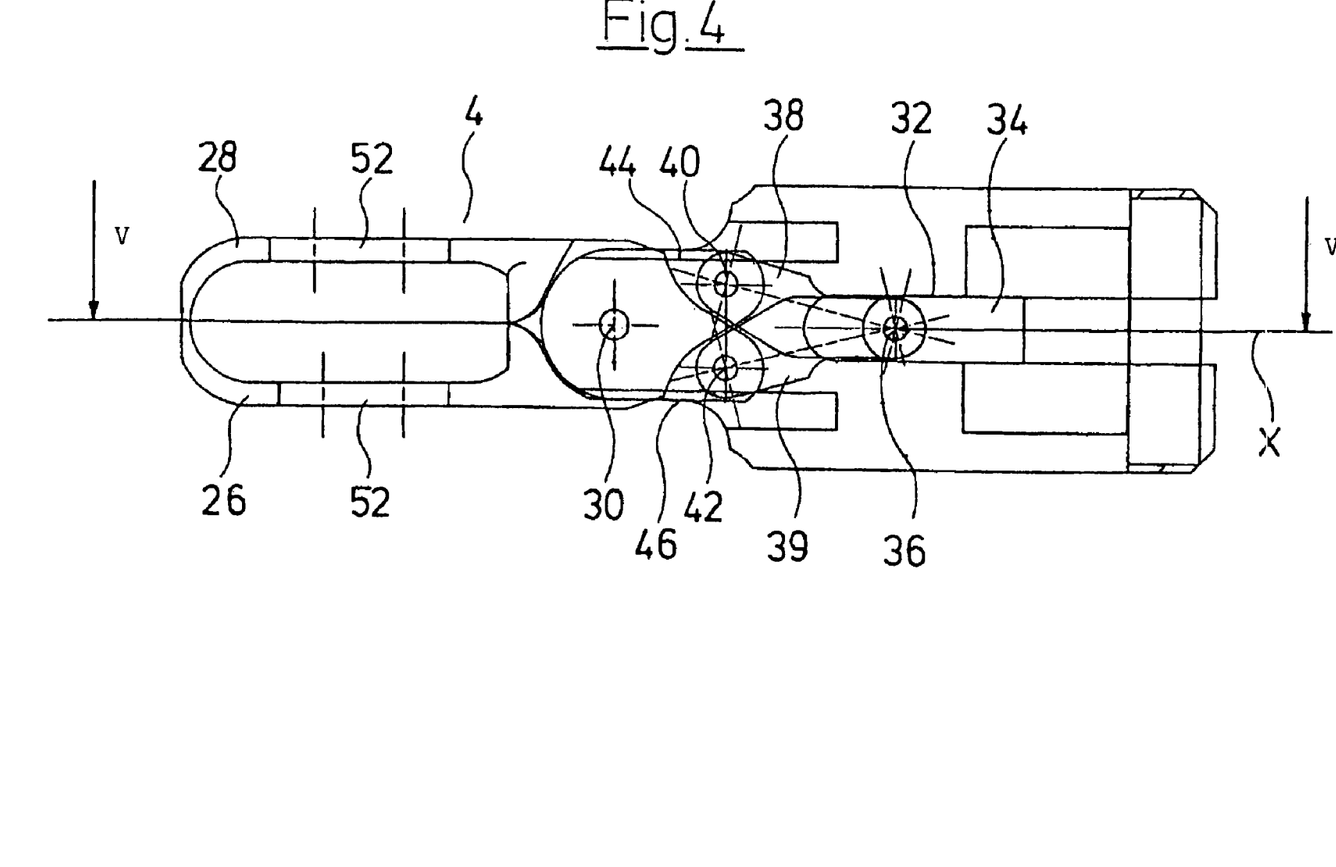
FIG. 4 is an enlarged schematic sectional view of the forceps jaw in the closed condition.

The exact construction of the lever system for actuating the jaw parts 26 and 28 is explained in more detail by way of the schematic representation in FIG. 4. The view in FIG. 4 corresponds essentially to the view according to FIG. 2, but the forceps jaw 4 is shown sectioned in order to show the individual lever elements. The jaw parts 26 and 28 are shown in the closed condition. Since the jaw parts 26, 28 are respectively linked and mounted on two diametrically opposite sides of the forceps shank 2, all lever and actuation elements are formed in an identical manner on the two diametrically opposite sides of the forceps shank 2. For this reason, the design on one of the two sides is hereinafter explained, the lever elements on the opposite side being designed identically. The projection 34, which is axially movable in the longitudinal direction of the forceps shank 2 in the longitudinal groove 32, is rigidly connected to the inner shank 10 (not shown in FIG. 4). A linkage point 36 is formed on the projection 34. The two transmission levers 38 and 39 are pivotably linked or mounted on this linkage point 36. For this purpose, there is provided a bore respectively in each of the projection 34 and the transmission levers 38, 39 through which there extends a rivet or bearing bolt. The transmission levers 38 and 39 are designed bent at an angle, so that in the installed condition they are bent at an angle respectively in two opposite directions to the longitudinal axis x or a plane through the longitudinal axis x and the rotation points 30. On ends of the transmission levers 38 and 39 which lie opposite the linkage points 36 there are provided rotation points 40 and 42 respectively. On account of the angled design of the transmission levers 38 and 39, the rotation points 40 and 42 lie outside the plane or axis which extends through the rotation points 30 and linkage points 36.

At the rotation points 40 and 42 the transmission levers 38 and 39 are rotatably connected to the jaw parts 26 and 28. This connection may likewise be achieved by bearing bolts or rivets, which are applied into corresponding holes in the transmission levers 38, 39 and the jaw parts 26, 28. The jaw parts 26 and 28 comprise linkage levers 44 and 46. The linkage lever 44 is formed as one piece with the jaw part 26, and the linkage lever 46 is formed as one piece with the jaw part 28. Proceeding from the associated jaw parts 26 and 28, the linkage levers 44 and 46 extend in the opposite direction, i.e., in the proximal direction of the forceps beyond the rotation points 30. At the same time, the linkage levers 44 and 46 are bent at an angle with respect to the respective associated jaw parts 26 and 28, in a manner such that the jaw part 26 is linked via the linkage lever 44 on the rotation point 40 on the side of the longitudinal axis x opposing or lying opposite the jaw part 26. Correspondingly, the jaw part 28 is linked via the linkage lever 46 on the rotation point 42 on the side of the longitudinal axis x which lies opposite the jaw part 28. In this manner, one creates a parallelogram mechanism, wherein the rotation points 40 and 42 are spaced from the x-axis in a direction perpendicular to this axis. This has the effect that the connection lines between the rotation points 40 and 42 and the rotation point 30, as well as the linkage point 36, run at angles to the rotational axis x. This ensures that with a movement of the linkage point 36 in the direction of the longitudinal axis in the distal direction, the two rotation points 40 and 42 are pressed apart by way of the transmission levers 38 and 39, so that they move away from one another. With this movement of the rotation points 40 and 42, the linkage levers 44 and 46 connected to these, and thus likewise the associated jaw parts 26 and 28, are pivoted about the rotation point 30, so that the forceps jaw 4 opens. The movement of the linkage point 36 in the longitudinal direction of the x-axis is effected by a movement of the inner shank 10 in its longitudinal direction, since the inner shank 10 is rigidly connected to the projection 34.

Figure 5:
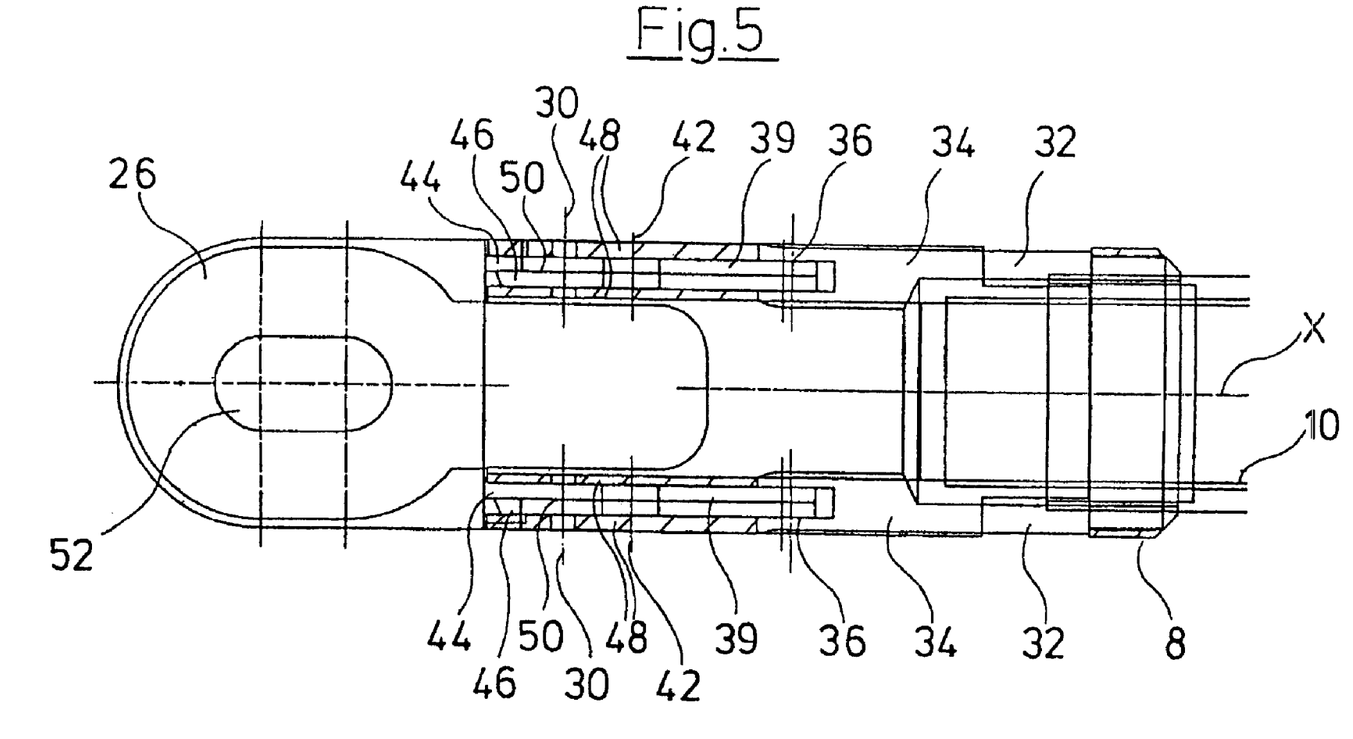
FIG. 5 is a view of the forceps jaw in the direction of the arrows V in FIG. 4.

FIG. 5 shows a sectional view of the forceps jaw according to FIG. 4 in the direction of the arrows V in FIG. 4. The distal end region 48 of the outer shank 8 forms, on each of the two diametrically opposite sides, a receiver gap 50, in which the linkage and transmission levers 44, 46 and 38 and 39, respectively, are arranged. The levers are arranged lying over one another or overlapping, in a manner such that the transmission lever 39 on one of the diametrically opposite sides lies radially further inward with respect to the longitudinal axis x than on the opposite side. Correspondingly, the associated linkage levers on one side are arranged lying further radially inward than on the other side. Thus the linkage and transmission levers 38, 39, 44 and 46, respectively, form an extremely flat parallelogram mechanism, which is arranged in the respective receiver gaps 50. For its design also one of the linkage levers 44 or 46 on the respective jaw parts 26 and 28 is situated lying further inward with respect to the longitudinal axis x on one side than on the diametrically opposite side. On the side on which the linkage lever 46 lies further outward, the associated transmission lever 39 lies further inward, and on the side on which the linkage lever 46 lies further inward, the associated transmission lever 39 lies further outward. This correspondingly applies to the linkage levers 44 of the jaw part 26 and the associated transmission levers 38. The linkage levers 44, 46 and transmission levers 38, 39 are arranged respectively parallel to one another and lying over one another or overlapping in the receiver gaps 50.

Figure 6:
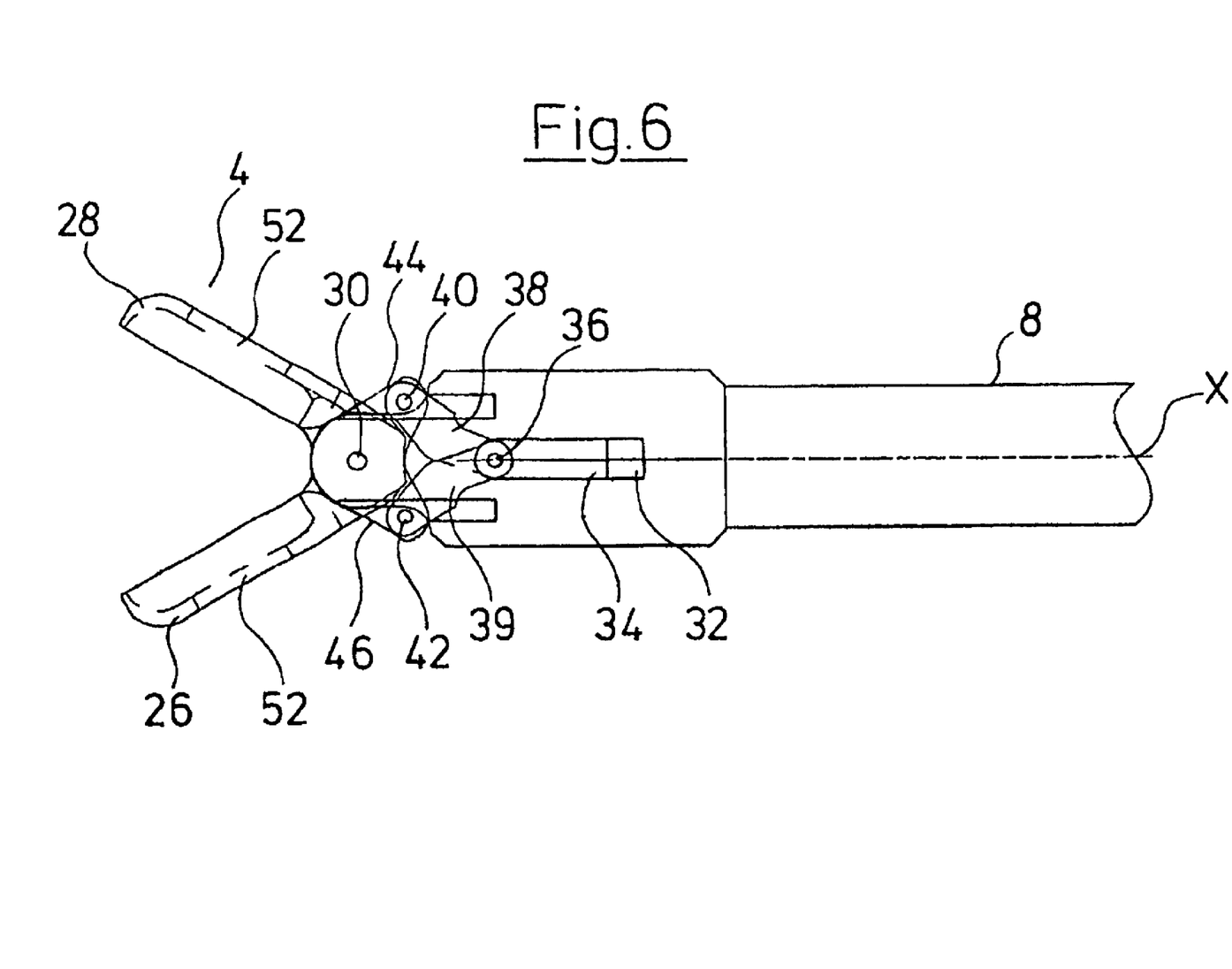
FIG. 6 is a view of the forceps jaw according to FIG. 4 in the open condition.

FIG. 6 shows a view according to FIG. 4 in which the forceps jaw 4 is open. As already explained by way of FIG. 4, for opening the forceps jaw 4 the inner shank 10 (not shown in FIG. 6) is moved inside the outer shank 8 along the longitudinal axis in the direction of the distal end of the forceps, i.e., in the direction of the forceps jaw 4. At the same time, on each of the diametrically opposite sides, the projection 34 with the linkage point 36 likewise moves in the direction of the distal end. In this manner, the transmission levers 38 and 39 on each side are pressed outward, so that the rotation points 40 and 42 move away from one another. Since the linkage levers 44 and 46 are rotatably connected to the transmission levers at the rotation points 40 and 42, with this movement the linkage levers 44 and 46 are rotated about the respective rotation points 30. At the same time, the jaw parts 26 and 28 are likewise rotated about both rotation points 30, so that the forceps jaw opens 4.

Figure 7:
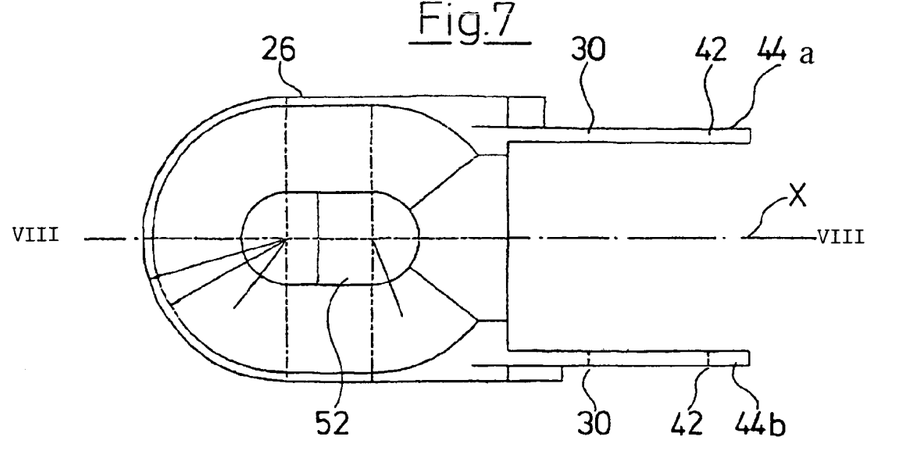
FIG. 7 is a detailed view of a forceps jaw in a plan view.

FIG. 7 shows an individual view of a jaw part 26. The jaw part 28 is designed identically to the jaw part 26. The jaw part 26 is shell-shaped, wherein at the lowest point there is formed an opening 52. When the forceps jaw is closed, the opening 52 permits one to observe the region of the surroundings of the forceps jaw 4 through the inside of the forceps jaw 4 and through the hole. The linkage levers 44 extend in the proximal direction at the distal end of the jaw part 26. The linkage levers 44 extend parallel to the longitudinal axis x. In the linkage levers 44 there are formed suitable bores for the rotation points 30 and 42 for connecting to the outer shank 8 and the transmission levers 39. The two linkage levers 44 are formed on two diametrically opposite sides of the jaw part 26. At the same time, on one side the linkage lever 44a lies further inside, i.e. closer to the longitudinal axis x than the linkage lever 44b on the diametrically opposite side. This formation permits the displaced overlapping arrangement of linkage and transmission levers. The transmission levers 46 on the second jaw part 28 are designed identically.

Figure 8:
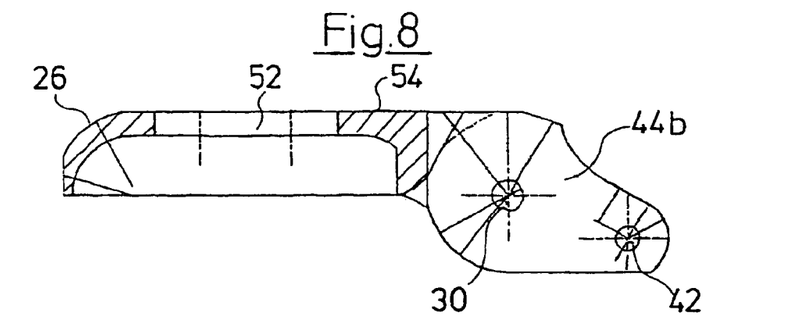
FIG. 8 is a sectional view of a jaw part along the line VIII—VIII in FIG. 7.

FIG. 8 shows a sectional view of the jaw part 26 according to FIG. 7 along line VIII—VIII in FIG. 7. In FIG. 8 the shell-shaped design of the jaw part 26 can be seen, wherein the opening 52 is arranged at the lowest point, i.e., at that point which lies farthest from the middle axis of the forceps shank 2. The linkage lever 44 or 44b is designed bent at an angle to the jaw part 26, so that the rotation point 42 is spaced further radially from the outer side 54 of the jaw part 26 than the rotation point 30. This permits the two jaw parts 26 and 28 to be arranged over one another in a manner such that they are rotatable about the same common rotation point 30 at the cross over of the two linkage levers 44 and 46. In this manner, one may create the parallelogram mechanism explained by way of FIG. 4, which permits a secure actuation of the forceps jaw 4 without danger of any jamming.

Figure 9:
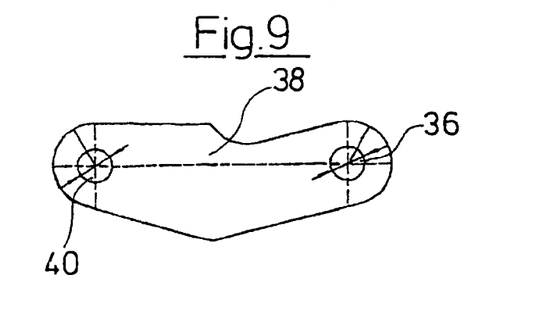
FIG. 9 is a detailed view of a deflection lever.

FIG. 9 shows a detailed view of a transmission lever 38. The transmission lever 38 at one end comprises an opening or bore for the rotation point 40 and at the opposite end an opening or bore for the linkage point 36. Bearing and joint bolts or rivets may extend through these holes. The linkage lever 38 has a bent configuration, as explained by way of FIG. 4.

As a whole, the medical forceps according to the invention has an extremely slim arrangement of all mounting and actuation elements for the forceps jaw 4 on two diametrically opposite sides of the forceps shank 2. In particular, the actuation elements, i.e., the linkage levers 44, 46 and the transmission levers 38, 39 are respectively arranged in the same circumferential region as the rotation points 30 on which the jaw parts 26 and 28 are mounted. In this manner, the circumferential regions which are required for mounting and linkage of the jaw parts 26 and 28 on the forceps shank 2 may be designed very slim in profile, so that in the remaining circumferential region, the field of view S of optics 12 arranged in the forceps shank is not limited. Furthermore, the linkage of the jaw parts on both sides permits the production of a large clamping force of the forceps, wherein both jaw parts 26, 28 are guided in a torsionally stiff manner.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A medical forceps comprising a tubular outer shank on whose distal end there is a forceps jaw with two jaw parts, each of the two jaw parts being rotatably mounted on each of two sides of the outer shank diametrically opposite one another, a tubular inner shank for actuating the jaw parts, the inner shank being displaceably arranged inside the outer shank in its longitudinal direction x, the inner shank being coupled to the two jaw parts for their actuation via two lever systems, and a first of the two lever systems being located on a first of the two sides of the outer shank diametrically opposite one another and being directly linked to both jaw parts, and a second of the two lever systems being located on a second of the two sides of the outer shank diametrically opposite one another and being directly linked to both jaw parts.

2. The medical forceps according to claim 1, wherein the two jaw parts each comprise two linkage levers, a first of the linkage levers of each jaw part being located on the first of the two sides of the outer shank diametrically opposite one another and a second of the linkage levers of each jaw part being located on the second of the two sides of the outer shank diametrically opposite one another, the linkage levers extending proximally in the longitudinal direction of the outer shank, the first of the linkage levers of each jaw part being connected to the inner shank via the first of the two lever systems and the second of the linkage levers of each jaw part being connected to the inner shank via the second of the two lever systems.

3. The medical forceps according to claim 2, wherein the tubular inner shank has an inner circumference, and wherein the linkage levers and the lever systems are arranged lying further radially outward than the inner circumference of the inner shank.

4. The medical forceps according to claim 2, wherein the two lever systems each comprise a transmission lever for connecting one of the linkage levers to the inner shank.

5. The medical forceps according to claim 4, wherein the transmission levers are each rotatably connected at a first end to a linkage lever and at a second end to the inner shank.

6. The medical forceps according to claim 5, wherein the transmission levers are connected to the inner shank at respective common rotation points on two sides of the inner shank diametrically opposite one another.

7. The medical forceps according to claim 4, wherein the respective transmission levers on each of the two sides of the outer shank diametrically opposite one another are respectively arranged lying radially over one another.

8. The medical forceps according to claim 4, wherein linkage levers and transmission levers on each of the two sides of the outer shank diametrically opposite one another respectively form a flat parallelogram mechanism.

9. The medical forceps according to claim 8, wherein the flat parallelogram mechanism is respectively arranged in a receiver gap in a distal end region of the outer shank on each of the two sides of the outer shank diametrically opposite one another.

10. The medical forceps according to claim 2, wherein the linkage levers have a form such that one of the linkage levers of a first jaw part lies radially further inward than one of the linkage levers of a second jaw part.

11. The medical forceps according to claim 2, wherein the linkage levers have a form such that, seen in the longitudinal direction of the outer shank in a closed condition of the forceps jaw, a free end of one of the linkage levers of a first jaw part extends in an extension of a second jaw part and a free end of one of the linkage levers of the second jaw part extends in an extension of the first jaw part.

12. The medical forceps according to claim 1, wherein each of the two jaw parts is mounted on each of the two sides of the outer shank diametrically opposite one another on respective common rotation points on the outer shank.

13. The medical forceps according to claim 1, wherein at a distal end of the inner shank at least one radially outwardly projecting projection engages into a corresponding recess at a distal end of the outer shank, and wherein the recess has a an elongated shape with its longer axis extending in the longitudinal direction of the outer shank.

14. The medical forceps according to claim 13, wherein there is one of the projections on each of the two sides of the inner shank diametrically opposite one another, and the outer shank comprises two of the corresponding recesses, one at each of the two sides of the outer shank diametrically opposite one another, into which the projections respectively engage.

15. The medical forceps according to claim 1, wherein at least one of the two jaw parts has an opening therein.

\* \* \* \* \*